US008957190B2

(12) United States Patent
Takakura et al.

(10) Patent No.: US 8,957,190 B2
(45) Date of Patent: Feb. 17, 2015

(54) USE OF HEAT-RESISTANT BIOTIN-BINDING PROTEIN, AND SOLID SUPPORT HAVING THE PROTEIN ATTACHED THERETO

(71) Applicant: Japan Tobacco Inc., Tokyo (JP)

(72) Inventors: Yoshimitsu Takakura, Iwata (JP); Satoru Usami, Iwata (JP); Masako Ichikawa, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 13/939,943

(22) Filed: Jul. 11, 2013

(65) Prior Publication Data

US 2013/0309691 A1 Nov. 21, 2013

Related U.S. Application Data

(62) Division of application No. 12/521,459, filed as application No. PCT/JP2007/075298 on Dec. 28, 2007, now abandoned.

(30) Foreign Application Priority Data

Dec. 28, 2006 (WO) .................. PCT/JP2006/326260

(51) Int. Cl.
*A23J 1/00* (2006.01)
*C07K 1/00* (2006.01)
*C07K 14/00* (2006.01)
*C07K 17/00* (2006.01)
*A23J 1/18* (2006.01)
*A61K 36/06* (2006.01)
*C07K 16/00* (2006.01)
*C07K 14/375* (2006.01)
*C07K 16/14* (2006.01)
*G01N 33/543* (2006.01)
*G01N 33/68* (2006.01)

(52) U.S. Cl.
CPC ............ *C07K 14/001* (2013.01); *C07K 14/375* (2013.01); *C07K 16/14* (2013.01); *G01N 33/543* (2013.01); *G01N 33/68* (2013.01); *G01N 2333/36* (2013.01)
USPC ............................ 530/412; 530/367; 530/371

(58) Field of Classification Search
None
See application file for complete search history.

(56) References Cited

U.S. PATENT DOCUMENTS

| | | | |
|---|---|---|---|
| 7,713,531 | B2 | 5/2010 | Takakura |
| 7,776,333 | B2 | 8/2010 | Takakura |
| 7,855,282 | B2 | 12/2010 | Takakura |
| 7,989,610 | B2 | 8/2011 | Takakura |
| 8,304,236 | B2 | 11/2012 | Takakura et al. |
| 2004/0077024 | A1 | 4/2004 | Holmberg |
| 2005/0089983 | A1 | 4/2005 | Takakura |
| 2009/0187006 | A1 | 7/2009 | Takakura |
| 2011/0263824 | A1 | 10/2011 | Takakura et al. |

FOREIGN PATENT DOCUMENTS

| | | |
|---|---|---|
| EP | 0456304 A1 | 11/1991 |
| WO | WO 99/60400 A1 | 11/1999 |
| WO | WO 02/072817 A1 | 9/2002 |

OTHER PUBLICATIONS

A print-out from http://www.gelifesciences.com/webapp/wcs/stores/servlet/catalog/en/GELifeSciences-US/brands/superoi Jul. 27, 2012.
Airenne, K.J., et al., "Production of Biologically Active Recombinant Avidin in Baculovirus-Infected Insect Cells," Protein Expression and Purification, vol. 9, 1997, pp. 100-106.
Airenne, K.J., et al., "Production of recombinant avidin in *Escherichia coli*," Gene. vol. 144, Feb. 21, 1994, pp. 75-80.
Diamandis et al., "The Biotin-(Strept)Avidin System: Principles and Applications in Biotechnology", Clinical Chemistry, vol. 37, No. 5 (1991) pp. 625-636.
European Search Report issued Feb. 2, 2011, in European Patent Application No. 07860501.
Green, M.N., "Avidin and Streptavidin," Methods Enzymol., vol. 184, 1990, pp. 51-67.
Green, M.N., "Avidin," Adv. Protein Chem., vol. 29, 1975, pp. 85-133.
International Search Report issued in PCT/JP2007/075298 on Mar. 4, 2008.
Mikayama et al., "Molecular cloning and functional expression of a cDNA encoding glycosylation-inhibiting factor", Proc. Natl. Acad. Sci. USA, vol. 90 (1993) pp. 10056-10060.
Sano, T., and Cantor, C.R., "Expression of a cloned streptavidin gene in *Escherichia coli*," Proc. Natl. Acad. Sci. USA, Jan. 1990, pp. 142-146.
Takakura et al., "Tamavidin, a versatile affinity tag for protein purification and immobilization," Journal of Biotechnology, vol. 145 (2010) pp. 317-322.
Takakura et al., "Tamavidins—novel avidin-like biotin-binding proteins from Tamogitake mushroom," FEBS Journal, vol. 276 (2009) pp. 1383-1397.

*Primary Examiner* — Suzanne M Noakes
*Assistant Examiner* — Gerard Lacourciere
(74) *Attorney, Agent, or Firm* — Birch, Stewart, Kolasch & Birch, LLP.

(57) ABSTRACT

The present invention relates to a solid support having a heat-resistant biotin-binding protein attached thereto. The present invention also relates to the use of the solid support of the present invention having a heat-resistant biotin-binding protein attached thereto. The present invention further relates to technical fields such as purification, concentration, detection and/or capture of a biotin-linked substance by means of a heat-resistant biotin-binding protein. Such a biotin-binding protein used in the solid support of the present invention is heat-resistant and is therefore useful for use in assay systems involving exposure to a temperature of 70° C. or more.

6 Claims, 6 Drawing Sheets

USE OF HEAT-RESISTANT BIOTIN-BINDING PROTEIN, AND SOLID SUPPORT HAVING THE PROTEIN ATTACHED THERETO

This application is a Divisional of copending application Ser. No. 12/521,459 filed on Mar. 8, 2010, which is a National Phase of PCT International Application No. PCT/JP2007/075298 filed on Dec. 28, 2007, which claims the benefit to Patent Application No. PCT/JP2006/326260 filed on Dec. 28, 2006. The entire contents of all of the above applications is hereby incorporated by reference.

TECHNICAL FIELD

The present invention relates to a solid support having a heat-resistant biotin-binding protein attached thereto. The present invention also relates to the use of the solid support of the present invention. The present invention further relates to technical fields such as purification, concentration, detection and/or capture of a biotin-linked substance by means of a heat-resistant biotin-binding protein.

BACKGROUND ART

The affinity between avidin and biotin or between streptavidin and biotin is very high ($K_d$=10$^{-15}$ to 10$^{-14}$ M) and provides one of the strongest in vivo binary interactions. At present, avidin/streptavidin-biotin interaction is widely used in the field of biochemistry, molecular biology or medicine (Green, (1975), Adv. Protein Chem., 29: 85-133; Green, (1990), Methods Enzymol., 184: 51-67). Avidin is an albumen-derived basic glycoprotein and has an isoelectric point exceeding 10. Due to its high basicity or sugar chain, avidin involves a problem of non-specific binding to DNA or other molecules, which limits the use of avidin. On the other hand, streptavidin is derived from an actinomycete strain (*Streptomyces avidinii*), and it has an isoelectric point at around neutral pH and contains no sugar chain. These two proteins each form a tetramer and bind to one biotin molecule per subunit. Their molecular weight is around 60 kDa.

Tamavidin (tamavidin 1; SEQ ID NO: 2) is a third biotin-binding protein that was purified from an edible mushroom, *Pleurotus cornucopiae* var. *citrinopileatus*, as an antifungal protein against the rice blast disease pathogen *M. grisea*. This protein has also been determined for its gene structure (WO 02/072817). Its homolog (tamavidin 2; SEQ ID NO: 4) has also been identified from the same mushroom, and recombinant proteins have also been successfully produced (WO 02/072817). Tamavidin homolog can be readily produced by being expressed in *E. coli* cells and purified with an iminobiotin column. This is a great advantage over the production systems for avidin and streptavidin.

When avidin is expressed in *E. coli* cells, the yield of a soluble protein is as low as about 50 µg per 50 ml (Airenne et al., 1994, Gene, 144: 75-80). For this reason, insect cell systems using baculoviruses are used currently (Airenne et al., 1997, Protein exp. Purif., 9: 100-108). Likewise, when streptavidin is expressed in *E. coli* cells, the resulting recombinant protein will form an insoluble inclusion body. This inclusion body should be solubilized with a high concentration of guanidine hydrochloride, followed by stepwise removal of guanidine hydrochloride through dialysis to cause protein refolding, thereby obtaining a soluble and active recombinant streptavidin (Sano and Cantor, 1990, Proc. Natl. Acad. Sci. USA, 87: 142-146). In this way, the production of avidin and streptavidin requires a great amount of effort and time. In contrast, when a tamavidin homolog was expressed in *E. coli* cells, 1 mg recombinant protein was obtained per 50 ml culture. This corresponds to a high level of efficiency in the production of biotin-binding proteins, and indicates the potential usefulness of a tamavidin homolog protein.

In the fields of reagents and diagnostic agents, there have been developed solid supports (e.g., magnetic beads, microplates or sensor chips) having avidin or streptavidin attached thereto. However, there is no report of such solid supports with low levels of non-specific binding and with high stability at a higher temperature range.

Patent Document 1: International Publication No. WO 02/072817

Non-patent Document 1: Green, 1975, Adv. Protein Chem., 29: 85-133

Non-patent Document 2: Green, 1990, Methods Enzymol., 184: 51-67

Non-patent Document 3: Airenne et al., 1994, Gene, 144: 75-80

Non-patent Document 4: Airenne et al., 1997, Protein exp. Purif., 9: 100-108

Non-patent Document 5: Sano and Cantor, 1990, Proc. Natl. Acad. Sci. USA, 87: 142-146

DISCLOSURE OF THE INVENTION

Problems to be Solved by the Invention

An object of the present invention is to provide a solid support having a heat-resistant biotin-binding protein attached thereto. Another object of the present invention is to provide a method for, e.g., purification, concentration, detection and/or capture of a biotin-linked substance by means of a heat-resistant biotin-binding protein. In this case, there is provided the use of the solid support of the present invention. Yet another object of the present invention is to provide a solid support having a biotin-binding protein attached thereto, which can be used in assay systems involving exposure to a high temperature of 70° C. or more.

Means for Solving the Problems

"Tamavidin" is a biotin-binding protein derived from a basidiomycete fungus, *Pleurotus cornucopiae* var. *citrinopileatus*, and there are two homologs, tamavidin 1 and tamavidin 2 (see WO 02/072817). As a result of extensive and intensive efforts, the inventors of the present invention have clarified that tamavidin 2 has a very high affinity to biotin, as in the case of conventionally-used avidin and streptavidin. Namely, the inventors have shown that tamavidin 2 and biotin have an affinity which is about 1.000-fold stronger than that obtained in many antigen-antibody reactions. The inventors have also demonstrated that tamavidin 2 is almost free from non-specific binding (to DNA), which binding is a problem with conventionally-used avidin. The inventors have further found that tamavidin 2 has a heat resistance which is 10° C. or more higher than in streptavidin, and have also found that this property is retained even after tamavidin 2 is attached to a solid support. As a result of further extensive and intensive efforts, the inventors of the present invention have found that tamavidin 1 strongly binds to biotin and has a heat resistance which is 5° C. higher than in streptavidin. Based on these studies, the inventors of the present invention have found that it is possible to provide a solid support having a heat-resistant biotin-binding protein attached thereto, which retains biotin-binding activity even under high temperature conditions. This finding led to the completion of the present invention. Accordingly, the present invention provides a solid support having a heat-resistant biotin-binding protein attached thereto, and the use thereof, as well as a method for purification, concentration, detection and capture of a biotin-linked substance by means of a heat-resistant biotin-binding protein.

The present invention will now be described in more detail below.

Solid Support Having a Heat-Resistant Biotin-Binding Protein Attached Thereto

The present invention provides a solid support having a heat-resistant biotin-binding protein attached thereto.

As used herein, the term "heat-resistant biotin-binding protein" is intended to mean tamavidin 1, tamavidin 2 or a mutant thereof. More specifically, the heat-resistant biotin-binding protein which is to be attached to the solid support of the present invention may be a protein comprising the amino acid sequence shown in SEQ ID NO: 2 or SEQ ID NO: 4, or a protein encoded by a nucleic acid comprising the nucleotide sequence shown in SEQ ID NO: 1 or SEQ ID NO: 3. Alternatively, the heat-resistant biotin-binding protein which is to be attached to the solid support of the present invention may be a mutant of a protein comprising the amino acid sequence shown in SEQ ID NO: 2 or SEQ ID NO: 4, or a mutant of a protein encoded by a nucleic acid comprising the nucleotide sequence shown in SEQ ID NO: 1 or SEQ ID NO: 3, wherein said mutant has the same biotin-binding activity and heat resistance as tamavidin 1 or 2. Tamavidin 1, tamavidin 2 and mutants thereof are also collectively and simply referred to as tamavidin.

Such a mutant of tamavidin 1 or 2 may be a protein which comprises an amino acid sequence comprising deletion, substitution, insertion and/or addition of one or more amino acids in the amino acid sequence shown in SEQ ID NO: 2 or 4 and which has the same biotin-binding activity and heat resistance as tamavidin 1 or 2. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Mutants derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis. As used herein, the term "one or more amino acids" may also be intended to mean one or several amino acids in some cases.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The mutant of tamavidin 1 or 2 may further be a protein which comprises an amino acid sequence sharing an amino acid identity of at least 60% or more, preferably 65% or more, 70% or more, 75% or more, 80% or more, 85% or more, 90% or more, 95% or more, 98% or more, 99% or more, and more preferably 99.3% or more with the amino acid sequence shown in SEQ ID NO: 2 or 4 and which has the same biotin-binding activity and heat resistance as tamavidin 1 or 2.

The percent identity between two amino acid sequences may be determined by visual inspection and mathematical calculation. Alternatively, the percent identity of two protein sequences may be determined by comparing sequence information based on the algorithm of Needleman, S. B. and Wunsch, C. D. (J. Mol. Biol., 48:443-453, 1970) and using the GAP computer program available from the University of Wisconsin Genetics Computer Group (UWGCG). The preferred default parameters for the GAP program include: (1) a scoring matrix, blosum62, as described by Henikoff, S. and Henikoff, J. G. (Proc. Natl. Acad. Sci. USA, 89:10915-10919, 1992); (2) a gap weight of 12; (3) a gap length weight of 4; and (4) no penalty for end gaps.

Other programs used by those skilled in the art of sequence comparison may also be used. The percent identity can be determined by comparing sequence information using, e.g., the BLAST program described by Altschul et al. (Nucl. Acids. Res., 25, p. 3389-3402, 1997). This program is available on the Internet at the web site of the National Center for Biotechnology Information (NCBI) or the DNA Data Bank of Japan (DDBJ). The details of various conditions (parameters) for identity search using the BLAST program are shown on these web sites, and default values are commonly used for search although part of the settings may be changed as appropriate. Alternatively, the percent identity of two amino acid sequences may be determined by using a program such as genetic information processing software GENETYX Ver. 7 (Genetyx Corporation, Japan) or using an algorithm such as FASTA. In this case, default values may be used for search.

The percent identity between two nucleic acid sequences can be determined by visual inspection and mathematical calculation, or more preferably, the comparison is done by comparing sequence information using a computer program. An exemplary, preferred computer program is the Genetic Computer Group (GCG; Madison, Wis.) Wisconsin package version 10.0 program, "GAP" (Devereux et al., 1984, Nucl. Acids Res., 12:387). In addition to making a comparison between two nucleic acid sequences, this "GAP" program can be used for comparison between two amino acid sequences and between a nucleic acid sequence and an amino acid sequence. The preferred default parameters for the "GAP" program include: (1) the GCG implementation of a unary comparison matrix (containing a value of 1 for identities and 0 for non-identities) for nucleotides, and the weighted amino acid comparison matrix of Gribskov and Burgess, Nucl. Acids Res., 14:6745, 1986, as described by Schwartz and Dayhoff, eds., "Atlas of Polypeptide Sequence and Structure," National Biomedical Research Foundation, pp. 353-358, 1979, or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website: http://www.ncbi.nlm.nih.gov/blast/bl2seq/bls.html, or the UW-BLAST 2.0 algorithm. Standard default parameter settings for UW-BLAST 2.0 are described at the following Internet site: http://blast.wustl.edu. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The mutant of tamavidin 1 or 2 may also be a protein which is encoded by a nucleic acid comprising a nucleotide sequence hybridizable under stringent conditions with the complementary strand of the nucleotide sequence shown in SEQ ID NO: 1 or 3 and which has the same biotin-binding activity and heat resistance as tamavidin 1 or 2.

The term "under stringent condition" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SCC to 0.2× SSC, preferably 6×SCC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH$_2$PO$_4$, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

The mutant of tamavidin 1 or 2 can be measured for its biotin-binding activity and heat resistance by any known procedure, for example, by the method using fluorescent biotin as described by Kada et al. (Biochim. Biophys. Acta., 1427: 44-48 (1999)). This method is an assay system based on the property of fluorescent biotin to lose its fluorescence intensity when bound to a biotin-binding site in a biotin-binding protein. Alternatively, it is also possible to evaluate the mutant protein for its biotin-binding activity by using a sensor which is capable of measuring protein-biotin binding, such as a biosensor designed on the principle of surface plasmon resonance. Heat resistance may be evaluated by varying the measurement temperature during evaluation of biotin-binding activity as described above.

The heat-resistant biotin-binding protein which is to be attached to the solid support of the present invention has a high affinity to biotin, and its dissociation constant K, is in the order of $10^{-8}$ M or less, preferably in the order of $10^{-9}$ M or less, in the order of $10^{-10}$ M or less, in the order of $10^{-11}$ M or less, in the order of $10^{-12}$ M or less, or in the order of $10^{-13}$ M or less. Typically, the dissociation constant $K_d$ may be in the order of $10^{-13}$ to $10^{-9}$ M.

The heat-resistant biotin-binding protein which is to be attached to the solid support of the present invention has higher heat resistance than known albumen-derived avidin or streptavidin. As used herein, the term "heat resistance" is intended to mean both protein stability at a higher temperature range and biotin-binding activity at a higher temperature range.

Protein stability at a higher temperature range may be evaluated as a temperature which causes a 50% reduction in protein band intensity compared to the room temperature value in SDS-PAGE analysis. For the heat-resistant biotin-binding protein which is to be attached to the solid support of the present invention, the temperature which causes a 50% reduction in protein band intensity compared to the room temperature value in SDS-PAGE analysis is higher than 71° C. and preferably may be 75° C. or more, 77.5° C. or more, 80° C. or more, 82.5° C. or more, 85° C. or more, or 87° C. or more.

Biotin-binding activity at a higher temperature range may be evaluated as a temperature which causes a 50% reduction in biotin binding compared to the room temperature value. For the heat-resistant protein which is to be attached to the solid support of the present invention, the temperature which causes a 50% reduction in biotin binding compared to the room temperature value is higher than 73° C. and preferably may be 75° C. or more, 78° C. or more, 80° C. or more, 82.5° C. or more, or 85° C. or more.

The heat-resistant biotin-binding protein which is to be attached to the solid support of the present invention may be purified from a protein of basidiomycete origin or may be obtained as a recombinant protein.

In the present invention, the solid support to which the heat-resistant biotin-binding protein is to be attached is not limited in any way, as long as it is a support which is solid or is made of an insoluble material (e.g., a material which can be separated from a reaction mixture by filtration, precipitation, magnetic separation or other techniques).

Examples of a material which constitutes the solid support include, but are not limited to, cellulose, Teflon™, nitrocellulose, agarose, dextran, chitosan, polystyrene, polyacrylamide, polyester, polycarbonate, polyamide, polypropylene, nylon, polydivinylidene difluoride, latex, silica, glass, glass fiber, gold, platinum, silver, copper, iron stainless steel, ferrite, silicon wafer, polyethylene, polyethyleneimine, polylactic acid, resins, polysaccharides, proteins (e.g., albumin), carbon or combinations thereof.

The solid support may have any shape including, but not limited to, beads, magnetic beads, thin films, microtubes, filters, plates, microplates, carbon nanotubes, sensor chips, etc. Flat solid supports such as thin films or plates may be provided with pits, channels, filter bottoms or the like, as is known in the art.

In an embodiment of the present invention, magnetic beads may have a spherical diameter in the range of about 25 nm to about 1 mm. In a preferred embodiment, magnetic beads have a diameter in the range of about 50 nm to about 10 μm. The size of magnetic beads may be selected as appropriate for the intended purpose. Since some bacterial spores have a size in the order of about 1 μm, beads preferred to capture such spores have a diameter larger than 1 μm.

In an embodiment of the present invention, beads composed of highly-crosslinked spherical agarose (e.g., sepharose) may have a diameter in the range of about 24 μm to about 165 μm. In a preferred embodiment, highly-crosslinked spherical agarose beads have a diameter in the range of about 24 μm to about 44 μm. The size of highly-crosslinked spherical agarose beads may be selected as appropriate for the intended purpose.

Examples of a solid support having a hydrophobic surface include polystyrene latex beads such as those commercially available from Polysciences, Warrington, Pa. or Spherotech, Liberville, Ill.

Examples of a silica ($Si_2O$)-treated or silica ($SiO_2$)-based solid support include superparamagnetic silica beads which are available from Polysciences, Warrington, Pa. Such silica beads can be used for capture of nucleic acids (e.g., DNA). Alternatively, it is also possible to use M-280 commercially available from Dynal Biotech, etc.

Magnetic beads having a hydrophilic surface can be used for capture of proliferating bacterial cells, nucleic acids and other elements. Examples of such magnetic beads include beads commercially available under the name Biomag® carboxyl from Polysciences, Warrington, Pa. or beads named MC02N/2928 from Bangs Laboratory, Inc., Fishers, Ind. Alternatively, it is also possible to use M-270 commercially available from Dynal Biotech, etc.

Attachment of the heat-resistant biotin-binding protein to the solid support may be accomplished by using techniques for coupling between protein and solid support, which are known to those skilled in the art. For example, the solid support surface is modified such that carboxyl groups are exposed on the surface, and such a carboxyl group and an amino group in the protein are reacted by coupling reaction in the presence of a crosslinking reagent, 1-ethyl-3-(3-dimethylaminopropyl)carbodiimide (EDC), whereby the protein can be attached to the solid support. Alternatively, for example, a solid support whose surface carboxyl groups are converted into active esters by the action of N-hydroxysuccinimide (NHS) is mixed with the protein in a buffer (pH 6.5 to 9) containing no primary amino group, whereby a linkage can be established between carboxyl group on the solid support surface and amino group in the protein.

In another embodiment, the crosslinking reagent BS3 (bis[sulfosuccinimidyl]suberate) or DSS (disuccinimidyl suberate) may be used to establish a linkage between amino group on the solid support surface and amino group in the protein, or alternatively, the crosslinking reagent SPDP (N-succinimidyl 3-[2-pyridyldithio]propionate) or GMBS (N-(4-maleimidobutyryloxy)succinimide) may be used to establish a linkage between amino group on the solid support surface and thiol group in the protein.

The heat-resistant biotin-binding protein which is to be attached to the solid support of the present invention retains protein stability and biotin-binding activity at a higher temperature range. For this reason, the solid support of the present invention can be treated while retaining its biotin-binding capacity at a higher temperature than in streptavidin conventionally most often used. The solid support of the present invention can be used while retaining its biotin-binding capacity, even when treated by exposure to heating conditions of 70° C. to 90° C., preferably 75° C. to 90° C., 80° C. to 90° C., 85° C. to 90° C., 70° C. to 85° C., 70° C. to 80° C., 75° C. to 80° C., 75° C. to 85° C., or 75° C. to 87.5° C. This means, for example, allowing formation of nucleic acid hybrids at a higher temperature and the subsequent washing, i.e., allowing hybridization at higher stringency. The solid support of the present invention enables the construction of an assay system which minimizes non-specific hybrid formation. Alternatively, for example, for attachment of tamavidin to the solid support, it is also possible to select a method in which high temperature treatment is imperative. Moreover, a more specific reaction can also be effected at high temperature for attachment of tamavidin to an element such as a heat-resistant protein, an enzyme or a fluorescent dye or for the subsequent reaction with a biotin-modified product.

Since the heat-resistant biotin-binding protein which is to be attached to the solid support of the present invention is almost free from non-specific binding to DNA, it is also possible to avoid the problem of non-specific binding to DNA, which problem is associated with avidin that is derived from albumen and is known in the art.

Method for Separation, Concentration, Purification Detection and or Capture of a Biotin-Linked Substance by Means of a Heat-Resistant Biotin-Binding Protein The present invention provides a method for separation, concentration, capture, purification and/or detection of a biotin-linked substance, which comprises the following steps:

1) contacting the tamavidin-attached solid support of the present invention with a biotin-linked substance, whereby the biotin-linked substance is bound to the solid support;

2) washing off contaminants which are not bound to the solid support; and 3) collecting the biotin-linked substance which is bound to the solid support to thereby separate, concentrate, capture or purify the substance and/or detect the substance. In a preferred embodiment, at least one of the above steps in the method of the present invention is accomplished under heating conditions of 70° C. to 90° C., more preferably under heating conditions of 75° C. to 90° C., 80° C. to 90° C., 85° C.

to 90° C., 70° C. to 85° C., 70° C. to 80° C., 75° C. to 80° C., 75° C. to 85° C., or 75° C. to 87.5° C.

In the method of the present invention, the term "biotin-linked substance" is intended to mean a substance linked with biotin either directly or indirectly. Direct linking between biotin and substance may be accomplished by covalent bonding. Indirect linking between biotin and substance may be accomplished by establishing a further linkage between the substance and a ligand covalently attached to biotin, through covalent bonding, ionic bonding, hydrogen bonding or hydrophobic interaction. Specific examples of indirect linking include conjugation of a biotinylated antibody to an antigen molecule through antigen-antibody reaction, as well as conjugation of a biotinylated nucleic acid probe to its complementary nucleic acid through nucleic acid hybridization.

In a preferred embodiment, at least one of the steps in the method of the present invention is accomplished under heating conditions of 70° C. to 90° C. It is therefore desired that indirect linking between biotin and substance should be retained under the temperature conditions used in the method of the present invention. For example, in a case where nucleic acid hybridization is used for indirect linking between biotin and substance, the length of a nucleotide sequence to be hybridized may be at least 20 nucleotides or more, preferably at least 25 nucleotides or more, 30 nucleotides or more, 35 nucleotides or more, 40 nucleotides or more, 50 nucleotides or more, or 100 nucleotides or more.

The material and shape of the tamavidin-attached solid support used in the method of the present invention may be selected depending on the properties of a substance to be separated, concentrated, purified, detected and/or captured.

Likewise, the composition of a buffer, the temperature to be applied and other conditions used in each step in the method of the present invention may be determined as appropriate by those skilled in the art, e.g., taking into account the properties of a substance to be separated. To detect the substance separated, concentrated, captured and/or purified by the method of the present invention, appropriate procedures may be selected by those skilled in the art depending on the properties of the substance.

The method of the present invention may be designed in accordance with, but not limited to, detection of nucleic acid (JP 2003-125800 A), apparatus and method for isolating a nucleic acid from a sample (Bortolin et al., WO2004/005553), method for amplification of nucleic acid: hybridization signal amplification method (HSAM) (Zhang et al., WO1998/004745), or concentration of virus or viral genome (Tamatsukuri, 2004, 1310 INDUSTRY, 21(8): 39-47). Alternatively, the method of the present invention can also be used for detection, capture and/or concentration of cells or microorganisms.

For example, when virus particles in the body fluid are concentrated, an analyte is first incubated in an appropriate buffer with a biotinylated antibody capable of specifically binding to a virus surface antigen. Antibody biotinylation may be accomplished, for example, by using a kit commercially available from Pierce or other manufacturers. Next, the tamavidin-attached solid support (e.g., magnetic beads) of the present invention is added and mixed. In the final step, virus-antibody-biotin-tamavidin-magnetic bead conjugates are aggregated with a magnet and the supernatant is removed off, followed by washing several times with an appropriate buffer. The magnet is then removed and the conjugates are suspended in a desired buffer to thereby complete virus concentration.

Alternatively, when viral genomic DNA in the body fluid is concentrated, an analyte is first introduced into a solution appropriate for virus particle disruption to extract genomic DNA from virus particles. If necessary, this genome is dissociated into single strands in an additional step. The viral genome is then incubated with a biotinylated product of single-stranded oligo DNA being complementary to a part of the viral genome and composed of several tens to several hundreds of nucleotides or with a biotinylated and heat-denatured product of double-stranded DNA having a strand complementary to a part of the viral genome and being composed of several tens to several hundreds of nucleotides, whereby the biotinylated oligo DNA and the viral genome are hybridized with each other. If the tamavidin-attached solid support of the present invention is used in this case, it is possible to apply a higher temperature than in conventional avidin- or streptavidin-attached solid supports, for example, a temperature range of 70° C. to 90° C., preferably 75° C. to 90° C., 80° C. to 90° C., 85° C. to 90° C., 70° C. to 85° C., 70° C. to 80° C., or alternatively, 75° C. to 80° C., 75° C. to 85° C., 75° C. to 87.5° C. Such a higher temperature, when applied as a hybridization temperature, prevents non-specific DNA binding and allows more specific viral genome concentration which minimizes contamination with any DNA other than the desired viral genome. Next, the tamavidin-attached solid support (e.g., magnetic beads) of the present invention is added to and mixed with the sample in a high temperature state (where the biotinylated oligo DNA specifically captures the viral genome). In the final step, viral genome-oligo DNA-biotin-tamavidin-magnetic bead conjugates are aggregated with a magnet and the supernatant is removed off, followed by washing several times with an appropriate buffer. The magnet is then removed and the conjugates are suspended in a desired buffer to thereby complete viral genome concentration. Subsequently, viral genome detection may be performed by PCR (Saiki et al. (1985) Science 230: 1350-1354) or other techniques. Tamavidin is highly heat-resistant in the absence of biotin when compared to conventionally-used avidin and streptavidin, and is also almost free from non-specific binding to DNA. Thus, tamavidin is preferred for specific concentration of DNA as described above, by way of example.

Advantages of the Invention

Tamavidin, which is to be attached to the solid support of the present invention, retains protein stability and biotin-binding activity at a higher temperature range. For this reason, the solid support of the present invention can be treated while retaining its biotin-binding capacity at a higher temperature than in streptavidin conventionally most often used. The solid support of the present invention enables the construction of an assay system which involves treatment at a higher temperature range.

BRIEF DESCRIPTION OF THE DRAWINGS

FIG. 2A shows the results of SDS-PAGE, and FIG. 2B is a graph showing the results quantified for the protein bands in SDS-PAGE.

EXAMPLES

Example 1

Tamavidin 2 (TM2)

1-1. Characterization of Tamavidin 2

Figure 1:
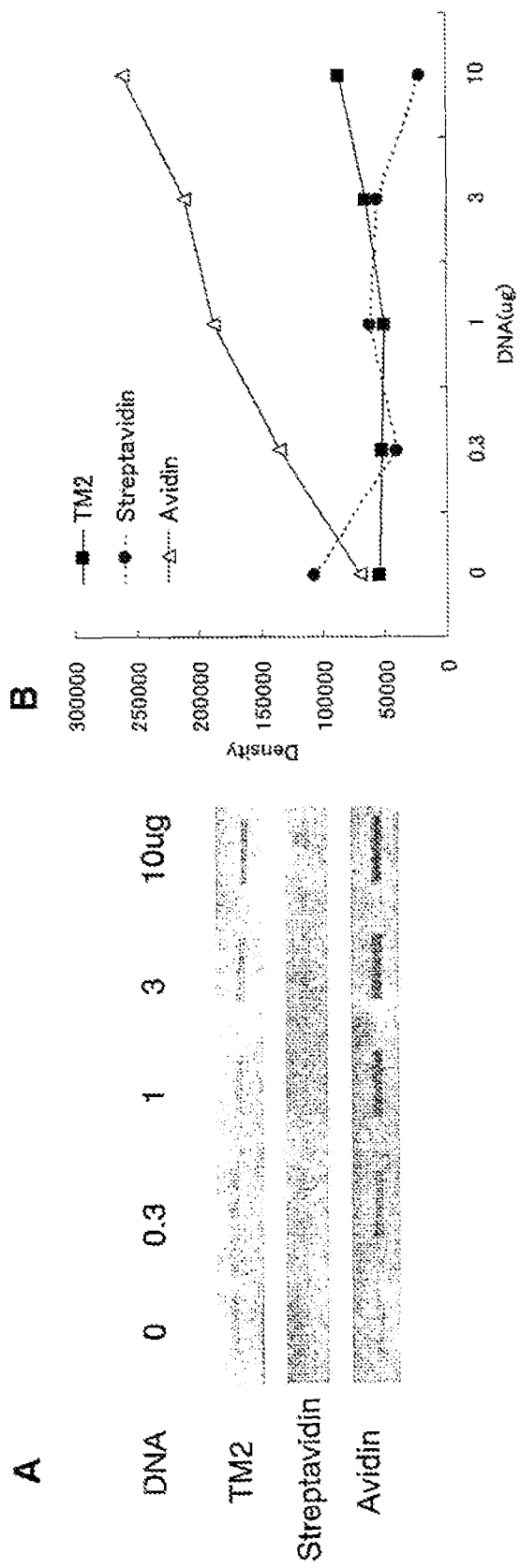
FIG. 1 presents a photograph (A) and a graph (B), each showing the results of tamavidin 2, streptavidin and avidin tested for their non-specific binding to DNA.

E. coli Expression and Purification of Tamavidin 2

When DNA encoding tamavidin 2 (TM2) (SEQ ID NO: 3) is integrated into an expression vector pTrc99A and expressed in E. coli cells, most of the expressed TM2 molecules are accumulated in a soluble fraction with high expression levels (WO 02/072817). TM2 protein was purified from recombinant E. coli cells according to the method of Hofmann et al. (Proc. Natl. Acad. Sci. USA, 77; 4666-4668, 1980) using a column filled with iminobiotin agarose (Sigma). More specifically, the E. coli cells described in WO 02/072817 were subjected to expression induction with 1 mM IPTG at 37° C. for 5 hours and then collected. The cell pellet was suspended in 50 mM Caps pH 11.0, 50 mM NaCl, followed by ultrasonication to disrupt the cells. After centrifugation, the supernatant was applied to a self-made iminobiotin column (height: 3 cm, volume: 0.5 ml) which had been equilibrated with 50 mM Caps pH 11.0, 50 mM NaCl. After washing with 5 ml of 50 mM Caps pH 11.0, 500 mM NaCl, the column was eluted with 1.5 to 2 ml of 50 mM $N_4$OAc pH 4.0. The yield of the purified protein was about 1 mg per 50 mL culture.

Mass Spectrometry

Tamavidin 2 was dissolved at a concentration of 10 mg/ml in 0.1% TFA, 50% MeCN saturated solution. This sample solution was purified with ZipTip C4 (Millipore) directly applied to a MALDI plate. The plate was air-dried and then overlaid with a matrix solution (sinapic acid). The plate was further air-dried and then mounted on a laser desorption/ionization time-of-flight mass spectrometer (MALDI-TOFMS) AXIMA-CFR (Shimadzu Corporation, Japan), followed by mass spectrometry (extraction voltage: 20 kV, flight mode: linear, detected ion: positive). The results observed were: m/z=15146.3 (monomer), 30335.0 (dimer) and 60932.0 (tetramer). Moreover, biotin-bound tamavidin 2 was found to show a larger peak corresponding to the tetramer. Based on these results, tamavidin 2 was determined to be a tetramer with a mass of 60932. N-terminal sequence analysis of this protein indicated that serine next to the translation initiation methionine was the N-terminal residue. The isoelectric point was calculated to be 7.36 for a polypeptide of tamavidin 2 composed of 140 amino acids excluding the initiation methionine, as analyzed by genetic information processing software GENETYX Ver. 7 (Genetyx Corporation, Japan).

Molar Absorption Coefficient

Tamavidin 2 has a theoretical molar absorption coefficient of $A_{280}=41750$ $M^{-1}$ $cm^{-1}$ $subunit^{-1}$ (0.68 at 0.25 mg/mL).

When tamavidin 2 was actually purified and dialyzed against ammonium acetate, the sample thus prepared had a weight of 3 mg after lyophilization (during which ammonium acetate was completely sublimated). This sample was dissolved in 20 mM KPi (pH 6.5), adjusted to a concentration of 0.25 mg/mL and then measured for $A_{280}$ to obtain a measured value of 0.67, which was 98% of the theoretical value. This indicated that the concentration of tamavidin can be easily determined by measurement of $A_{280}$.

Activity Measurement by Means of Fluorescent Biotin

By means of fluorescent biotin, tamavidin 2 was measured for its biotin-binding activity according to the method of Kada et al. (Biochim. Biophys. Acta., 1427: 44-48, (1999)). Solutions were prepared to contain the purified TM2 at stepwise concentrations from 0 pmol to 486 pmol in 200 μl assay buffer (50 mM $NaH_2PO_4$, 100 mM NaCl, 1 mM EDTA (pH 7.5)). These solutions were each mixed with 50 μL (1 nmol) of a 20 pmol/μL fluorescent biotin solution (biotin-4-fluorescein; Molecular Probe) and allowed to stand at room temperature for 10 minutes, followed by measuring the fluorescence intensity with a Las-3000 system (FUJIFILM). As a result, 0.274 nmol of TM2 was bound to nmol of fluorescent biotin. Namely, 3.6 mol of fluorescent biotin was bound to 1 mol of tamavidin. This indicated that 4 molecules of fluorescent biotin were bound per molecule of tamavidin (one molecule per subunit). In the case of streptavidin, 3.4 mol of fluorescent biotin was bound per mol of streptavidin.

1-2. Non-Specific Binding of Tamavidin 2 (TM2)

Purification of Rabbit Anti-TM2 Antibody

Tamavidin 2 (TM2) protein expressed in E. coli cells was purified with an iminobiotin column. Separately, the column-purified protein was further subjected to gel purification. The proteins thus purified were each used as an antigen to prepare two types of antibodies. The detection sensitivity in Western blotting with alkaline phosphatase-labeled anti-IgG antibody was about 0.5 ng for each purified recombinant tamavidin 2 preparation. Based on these results, it was concluded that antibodies with high specificity and high titer were completed. It should be noted that cross-reaction between anti-tamavidin 2 antibody and tamavidin 1 was detected, although at a low level (about 1/20 of that with the proper antigen).

The anti-TM2 antibody (which was prepared from the antigen purified only with an iminobiotin column) was further purified in the following manner. TM2 (40 μg) was separated by SDS-PAGE using two 15% acrylamide gels, and the protein was transferred onto two nitrocellulose membranes (BIO-RAD). The membranes were each blocked by shaking in TBS buffer containing 3% BSA at room temperature for 1 hour, and then reacted overnight at room temperature with the anti-TM2 antibody (which was prepared from the antigen purified only with an iminobiotin column, 1000-fold dilution). The site of each membrane where TM2 was transferred was excised and shaken in elution buffer (0.2 M glycine, 1 mM EDTA pH 2.8) at room temperature for 20 minutes. After neutralization with a 1 M Tris solution in a volume of 1/10 of the elution buffer, an equal volume of 10×TBS buffer was added for storage at 4° C.

Non-Specific Binding to DNA

Test on Tamavidin 2 (TM2) for Non-Specific Binding to DNA

TM2 was analyzed for its non-specific binding to DNA. Serial dilutions of salmon sperm DNA (10 μg to 0.3 μg) in 2×SSC buffer were alkali-denatured and adsorbed onto a Hybond N+ membrane (Amersham Biosciences) using Bio-Dot SF (BIO-RAD). The membrane was blocked with 5×Denhardt's solution (0.1% BSA, 0.1% Ficoll, 0, 1% polyvinylpyrrolidone) and then immersed in a 25 µg/mL TM2, streptavidin or avidin solution at room temperature for 90 minutes. The membrane was then washed three times with TTBS buffer (TBS buffer containing 0.05% Tween 20) at room temperature for 5 minutes. The membrane was blocked with TBS buffer containing 0.5% skimmed milk and 0.01% Tween 20 for 1 hour. The primary antibodies used were rabbit anti-TM2 antibody (purified as described above) for TM2, rabbit anti-streptavidin antibody (SIGMA) for streptavidin, and rabbit anti-avidin antibody (Abcam) for avidin, which were diluted to give the same antibody titer before use. Antigen-antibody reaction with each primary antibody was performed overnight at room temperature. The membrane was washed three times with TTBS buffer at room temperature for 5 minutes, and then reacted at room temperature for 1 hour with alkaline phosphatase-labeled anti-rabbit IgG antibody (BIO-RAD; 10000-fold dilution) as a secondary antibody. The membrane was washed three times with TTBS buffer at room temperature for 5 minutes, and then developed with an Alkaline Phosphatase substrate kit II, vector Black (Funakoshi Co., Ltd., Japan), followed by quantification with a Las-3000 system (FUJIFILM). As a result, avidin showed a DNA concentration-dependent increase in its staining intensity, whereas the staining intensity of TM2 and streptavidin was not strongly affected by DNA concentration (FIGS. 1A and 1B). This result indicated that tamavidin 2 was almost free from non-specific activity to DNA and was comparable to streptavidin. This demonstrates the superiority of tamavidin 2 over avidin.

1-3. Interaction Analysis Between Tamavidin 2 and Biotin

Kinetic Analysis of Tamavidin 2 (TM2)-Biotin Interaction Using a Biacore Biosensor Highly-purified BSA (2 mg, Sigma) and NHS-biotin (1 mg, Pierce) were dissolved in 1 ml of 50 mM sodium borate pH 8.0 and incubated at 4° C. for 2 hours. The NHS-biotin (EZ-Link NHS-LC-LC-Biotin) had been dissolved in a small volume of DMSO before addition. This solution was introduced into a dialysis tube (MWCO 6-8,000) and dialyzed overnight at 4° C. against 50 mM sodium carbonate pH 6.7. The biotin-BSA conjugate thus prepared (MW 67 kDa, 30 µM) was used as a ligand (a substance immobilized on a sensor chip) for a Biacore® biosensor. On the other hand, recombinant tamavidin 2 was prepared as an analyte (a substance flowing through channels) and analyzed for intermolecular interactions using a Biacore® 3000 (a biosensor designed on the principle of surface plasmon resonance, Biacore Inc.). Biotin-BSA and BSA alone (serving as a negative control) were each immobilized on CM5 sensor chips by amine coupling techniques. Their immobilized amount was adjusted to around 200 RU. BSA-immobilized chips were placed in flow cells 1 and 3, while biotin-BSA-immobilized chips were placed in flow cells 2 and 4. Tamavidin 2 was loaded into flow cells 1 and 2, while streptavidin was loaded into flow cells 3 and 4, each being loaded at a flow rate of 20 µl/min for 2 minutes in running buffer [10 mM HEPES pH 7.4, 150 mM NaCl, 3 mM EDTA, 0.005% Surfactant 20 (Biacore Inc.)]. The samples were then monitored for their dissociation over 60 minutes. It should be noted that since tamavidin 2 and streptavidin once bound were impossible to dissociate, the measurement was made at 7 concentrations starting from the lowest (3.125, 6.25, 12.5, 25, 50, 100 and 200 nM) without performing any regeneration step. The data of BSA was subtracted as the reference from the data of BSA-biotin. The measurement was made at 25° C. The resulting sensorgrams were each subjected to reaction kinetic analysis with the analysis software BIAevaluation ver. 4.1 in a 1:1 binding model to calculate the association rate constant ($k_a$) and the dissociation rate constant ($k_d$). The dissociation constant ($K_d$) was determined from $k_d/k_a$.

It should be noted that when the regeneration step was skipped, Rmax (the maximum binding amount of an analyte) was reduced ever time the measurement at each concentration was made. For this reason, Rmax was calculated by local fitting for each concentration during analysis. Moreover, only the data of analyte concentrations, which could be closely approximated to a 1:1 binding model, were selected for use.

The kinetic analysis results for intermolecular interaction between recombinant tamavidin 2 and biotin using a Biacore® 3000 (a biosensor designed on the principle of surface plasmon resonance) are as shown in Table 1 below.

TABLE 1

Kinetics of interaction between tamavidin 2 and biotin

| Protein | Molecular mass (kDa) | Association rate constant $k_s$ ($M^{-1}s^{-1}$) | Dissociation rate constant $k_d$ ($s^{-1}$) | Dissociation constant $K_d$ (M) |
|---|---|---|---|---|
| Tamavidin 2 | 61 | $9.19 \times 10^5$ | $6.83 \times 10^{-6}$ | $7.43 \times 10^{-12}$ |
| Streptavidin | 60 | $2.28 \times 10^6$ | $2.52 \times 10^{-6}$ | $1.11 \times 10^{-12}$ |

The dissociation constant obtained for tamavidin 2 was in the order of $10^{-12}$ M, which was in the same order as that of the dissociation constant measured for streptavidin in this test. This result indicated that tamavidin 2 is a protein having a very high affinity to biotin, ranking third after avidin and streptavidin. This suggests that tamavidin 2 is applicable to currently widely used avidin-biotin techniques.

1-4. Heat Resistance of Tamavidin 2

Tamavidin 2 (TM2) was analyzed for its heat resistance in comparison with streptavidin or avidin.

Figure 2:
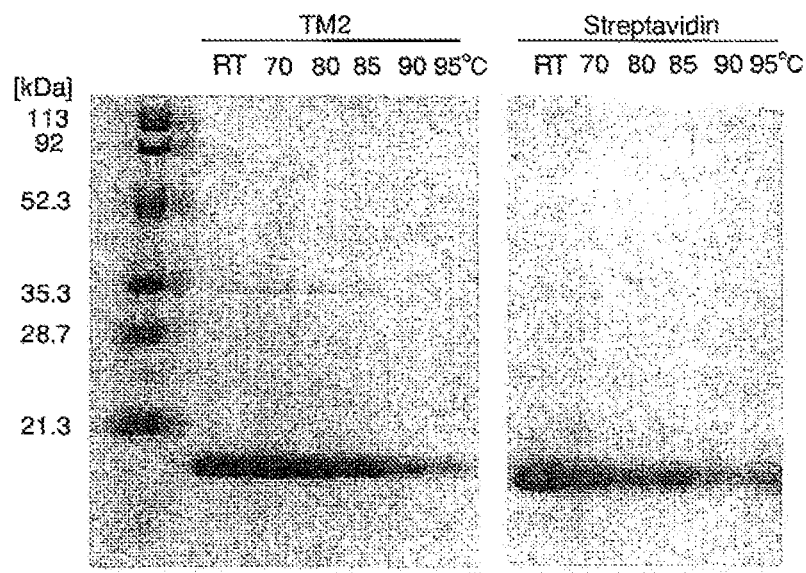
FIG. 2 shows the results of tamavidin 2 evaluated for its heat resistance (protein stability) in comparison with streptavidin.
Figure 2:
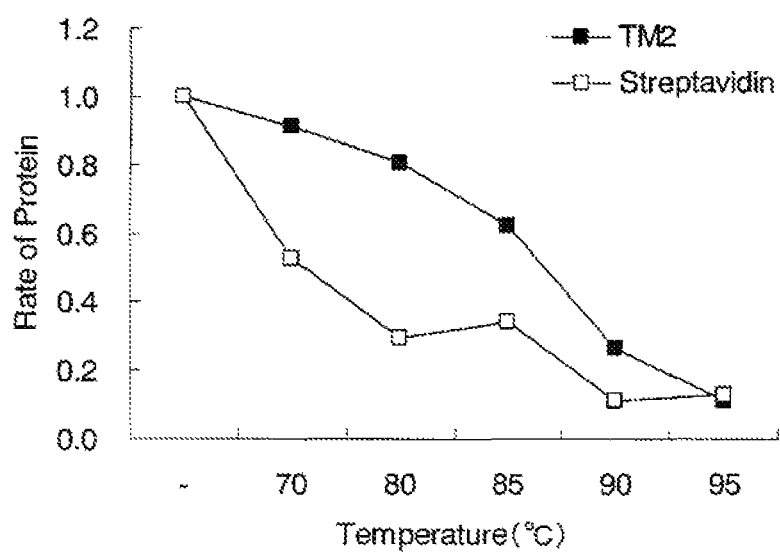

Protein Stability 0.2 µg/µL TM2 and 0.2 µg/µL streptavidin were heated in 10 µL (2 µg) volumes at room temperature, 50° C., 60° C., 70° C., 80° C., 90° C. or 99° C. for 20 minutes, followed by centrifugation at 15000 rpm for 10 minutes. Each supernatant (soluble protein) was suspended in an equal volume of 2×SDS sample buffer (100 mM Tris-HCl pH 6.8, 12% 2-mercaptoethanol, 2% SDS, 20% glycerol), heated at 95° C. for 10 minutes and then analyzed by SDS-PAGE. Protein bands were detected by CBB staining. Using a Las-3000 system (FUJIFILM), a calibration curve was prepared based on quantification markers (LMW ELECTROPHORESIS CALIBRATION KIT; Pharmacia Biotech) and used to quantify the protein bands. The results of SDS-PAGE are shown in FIG. 2A, while the results quantified for the protein bands are shown in FIG. 2B. The temperature which caused a 50% reduction in protein band intensity was 71° C. for streptavidin, whereas it was 87° C. for tamavidin 2. This result indicated that the heat resistance of tamavidin 2 was 15° C. more higher than that of streptavidin. Moreover, tamavidin 2 was found to show extremely high heat resistance upon addition of biotin, so that tetramer dissociation was not observed even after treatment at 95° C.

Biotin-Binding Activity

Based on the property of fluorescent biotin to lose its fluorescence intensity when bound to a biotin-binding site in a biotin-binding protein, tamavidin 2 was compared with streptavidin and avidin for biotin-binding capacity under high temperature conditions.

About 0.25 μg/μL TM2 and streptavidin were heated at room temperature, 50° C., 60° C., 70° C., 80° C. or 90° C. for 20 minutes. Solutions were prepared to contain the heat-treated TM2 or streptavidin at stepwise concentrations from 0 μL to 27 μL in 150 μL assay buffer (50 mM $NaH_2PO_4$, 100 mM NaCl, 1 mM EDTA (pH 7.5)). These solutions were each mixed with 50 μL (250 pmol) of a 5 pmol/μL fluorescent biotin solution (biotin-4-fluorescein; Molecular Probe) and allowed to stand at room temperature for 20 minutes, followed by measuring the fluorescence intensity with a Las-3000 system (FUJIFILM).

Heat resistance test on the biotin-binding proteins was accomplished as follows. About 0.25 μg/μL biotin-binding protein was heated at room temperature, 50° C., 60° C., 70° C., 80° C. or 90° C. for 20 minutes. Solutions were prepared to contain the heated biotin-binding protein at stepwise concentrations from 0 μL to 12 μL in 150 μL assay buffer. These solutions were each mixed with 50 μL (100 pmol) of a 2 pmol/μL fluorescent biotin solution and allowed to stand at room temperature for 20 minutes, followed by measuring the fluorescence intensity at Ex=460 nm and Em=525 nm with an Infinite M200 (TECAN).

Figure 3:
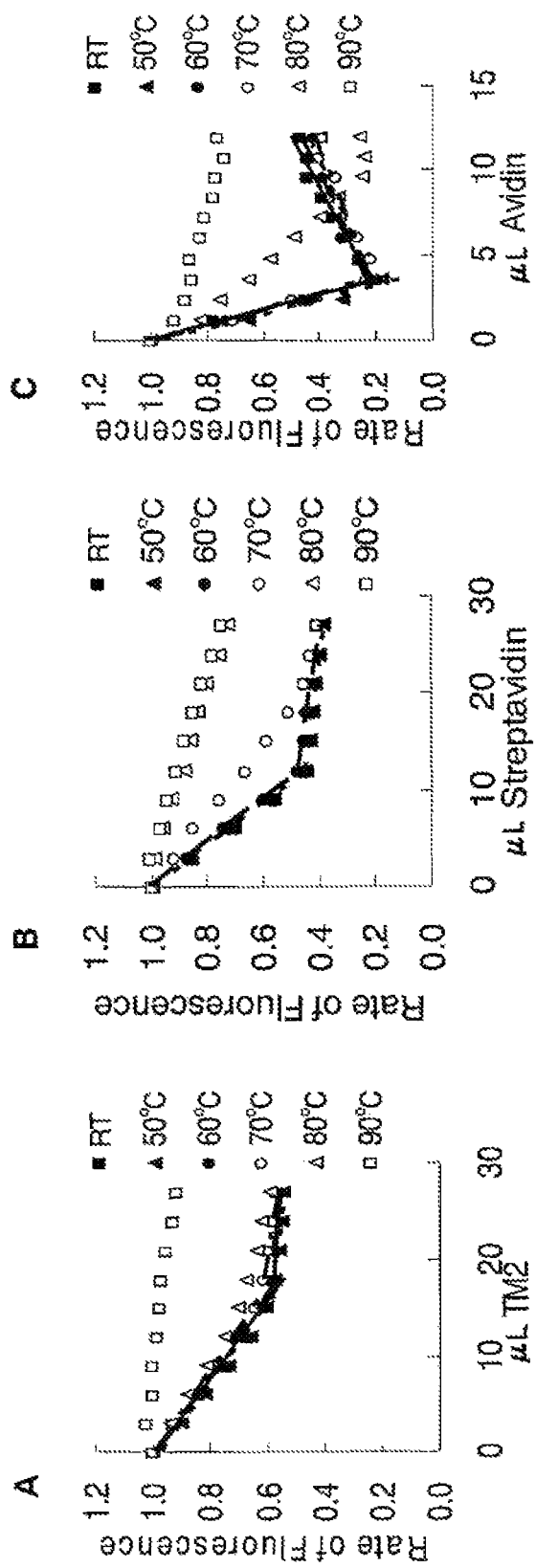
FIG. 3 presents graphs showing the heat resistance (fluorescent biotin-binding activity) of tamavidin 2 (A), streptavidin (B) and avidin (C).

The results obtained are shown in FIG. 3. As a result, TM2 showed no change in its binding to fluorescent biotin at 70° C. or below, compared to the room temperature value, and it retained 82% activity at 80° C. In contrast, the binding activity between streptavidin and fluorescent biotin was reduced by 40% at 70° C. and by 80% at 80° C. Likewise, the binding activity between avidin and fluorescent biotin was reduced by 10% at 70° C. and by 70% at 80° C. The temperature which caused a 50% reduction in fluorescence intensity decrement compared to the unheated sample was 85° C. for TM2, whereas it was 73° C. for streptavidin and 78° C. for avidin.

1-5. Heat Resistance of Tamavidin 2-Immobilized Support

Preparation of Tamavidin 2 Magnetic Beads

Magnetic beads whose surface was coated with carboxyl groups (300 μl; Dynabeads M-270 Carboxylic Acid, Dynal) were washed with 0.01 N sodium hydroxide (300 μl) for 10 minutes and then further washed three times with ultrapure water (300 μl) for 10 minutes. To the washed magnetic beads, 1-ethyl-3-(3-dimethylaminopropyl)carbodiimide hydrochloride (EDC) (PIERCE) dissolved in cold ultrapure water was added at a final concentration of 0.2 M and shaken for 30 minutes at room temperature. Then, the magnetic beads were washed sequentially with cold ultrapure water (300 μl) and 50 mM MES buffer (pH 5.0, 300 μl), and mixed with 300 μl (180 μg) of 0.6 mg/ml TM2 whose buffer had been replaced with 50 mM MES buffer (pH 5.0). By shaking at room temperature for 30 minutes, TM2 and the magnetic beads were covalently attached to each other. The magnetic beads were collected with a magnet and the supernatant was removed off. Then, unreacted carboxyl groups on the beads were eliminated with 50 mM Tris buffer (pH 7.0, 300 μl), and the magnetic beads were blocked with PBS buffer (300 μl) containing 0.5% BSA and 0.1% Tween 20. The magnetic beads were suspended in PBS buffer (300 μl) to complete the desired magnetic beads. Magnetic beads were also prepared for streptavidin and avidin in the same manner.

Heating Test on Tamavidin 2 Magnetic Beads (i) Heat Resistance

By means of fluorescent biotin, the heat resistance of TM2 magnetic beads was compared with that of the streptavidin magnetic beads and avidin magnetic beads prepared above, as well as with that of commercially available streptavidin magnetic beads (Dynabeads M-270 Streptavidin, Dynal).

Each type of magnetic beads was washed with PBS buffer and then heated at room temperature, 70° C., 75° C., 80° C., 85° C. or 90° C. for 20 minutes. Solutions were prepared to contain the heated magnetic beads at stepwise concentrations from 0 μL to 16 μL in 150 μL assay buffer. These solutions were each mixed with 50 μL (50 pmol) of a 1 pmol/μL biotin-4-fluorescein solution and allowed to stand at room temperature for 20 minutes, followed by measuring the fluorescence intensity of the supernatant at Ex=460 nm and Em=525 nm with an Infinite M200.

Figure 4:
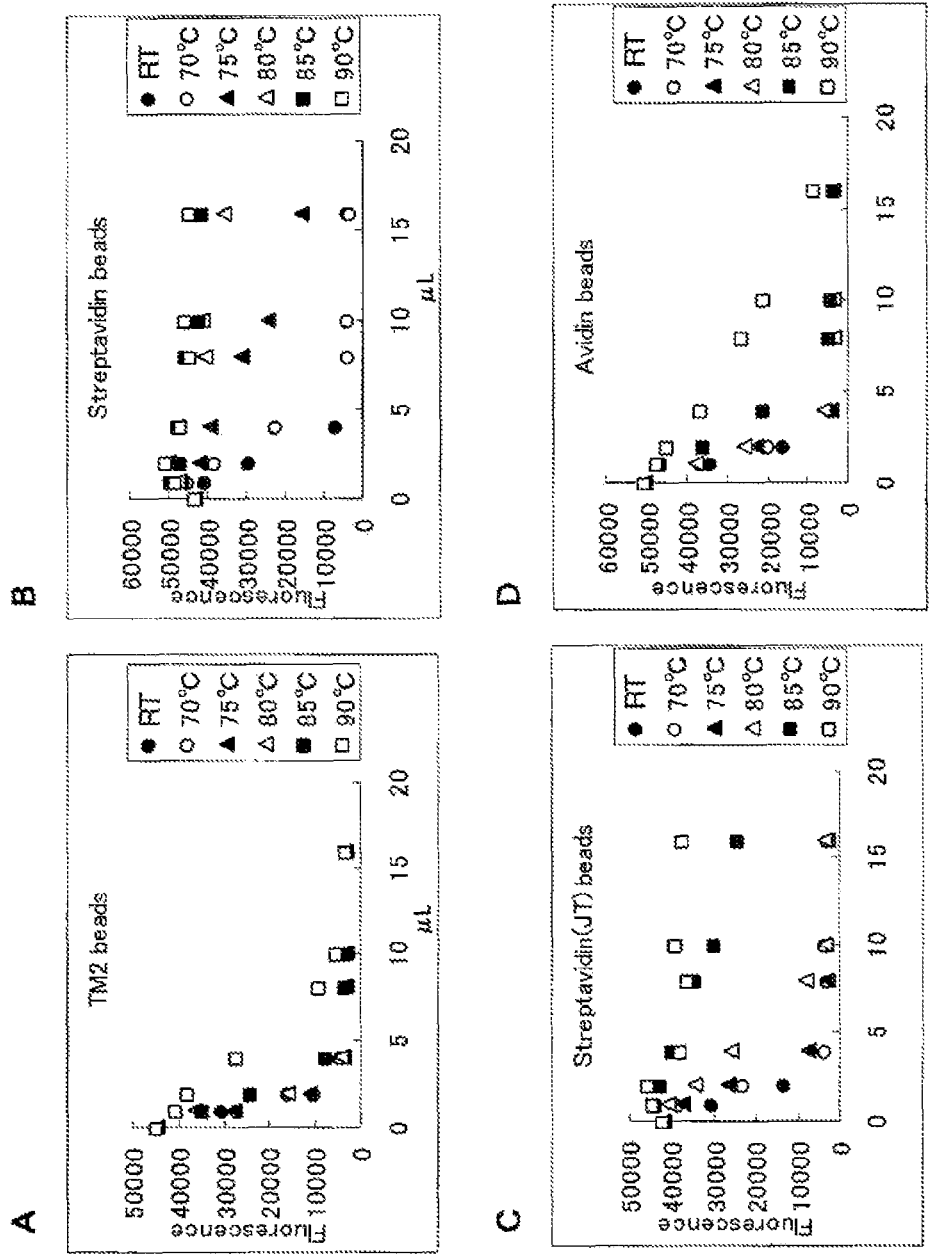
FIG. 4 presents graphs showing the heat resistance (fluorescent biotin-binding activity) of tamavidin 2 magnetic beads (A), commercially available streptavidin magnetic beads (B), streptavidin magnetic beads (C) and avidin magnetic beads (D).

The results obtained are shown in FIG. 4. As a result, the TM2 magnetic beads showed no change in their binding to fluorescent biotin at 75° C. or below, compared to the room temperature value, and they retained 73% activity at 80° C. and 64% activity at 85° C. The streptavidin magnetic beads were deactivated by 70% at 80° C., while the commercially available streptavidin magnetic beads (Dynal) were deactivated by 90% at 80° C. Likewise, the avidin magnetic beads were deactivated by 35% at 80° C. and by 55% at 85° C. The temperature which caused a 50% reduction in fluorescence intensity decrement compared to the unheated sample was 87° C. for TM2, whereas it was 78° C. for streptavidin, 72° C. for streptavidin (Dynal) and 84° C. for avidin.

(ii) Biotin-Binding Activity at a Higher Temperature Range

Based on the property of fluorescent biotin to lose its fluorescence intensity when bound to a biotin-binding site in a biotin-binding protein, TM2 magnetic beads were compared with commercially available streptavidin magnetic beads for biotin-binding capacity under high temperature conditions.

The TM2 magnetic beads were prepared by covalently attaching TM2 to magnetic beads whose surface was coated with carboxyl groups (Dynabeads M-270 Carboxylic Acid, Dynal). The commercially available streptavidin magnetic beads used were Dynabeads M-270 Streptavidin (Dynal). The TM2 magnetic beads are at $2 \times 10^9$ beads/30 mg/mL, and 333 pmol of fluorescent biotin is bound per mg of the magnetic beads. Likewise, the commercially available streptavidin magnetic beads are at $6.7 \times 10^8$ beads/10 mg/mL, and 625 pmol of fluorescent biotin is bound per mg of the magnetic beads.

The TM12 magnetic beads and commercially available streptavidin magnetic beads (300 μL each) were washed twice with PBS buffer (300 μL) and suspended again in PBS buffer (300 μL). Each type of magnetic beads was dispensed in 42 μL aliquots into 7 tubes. A 1 pmol/μL fluorescent biotin solution (biotin-4-fluorescein; Molecular Probe) was added in a volume of 50 μL (50 pmol) to 150, 149, 148, 146, 142, 140 or 134 μL of assay buffer (50 mM $NaH_2PO_4$, 100 mM NaCl, 1 mM EDTA (pH 7.5)) and pre-incubated at room temperature, 50° C., 60° C., 65° C., 70° C., 80° C. or 95° C. for 10 minutes. Subsequently, both types of magnetic beads were pre-incubated at room temperature, 50° C., 60° C., 65° C., 70° C., 80° C. or 95° C. for 5 minutes, 1, 2, 4, 8, 10 or 16 μL of which was then added to the 50 pmol fluorescent biotin solution to give a final volume of 200 μL, followed by heating at each temperature for 20 minutes. During heating, the mixture was suspended three times by pipetting. Then, the magnetic beads were quickly collected with a magnet, and the fluorescence intensity was measured for each supernatant at Ex=460 nm and Em=525 nm with an Infinite M200 (TECAN) (Experiment 1). In Experiment 2, the same procedure as used in Experiment 1 was repeated to analyze the binding capacity at room temperature, 70° C., 75° C., 80° C., 85° C. and 90° C.

Figure 5:
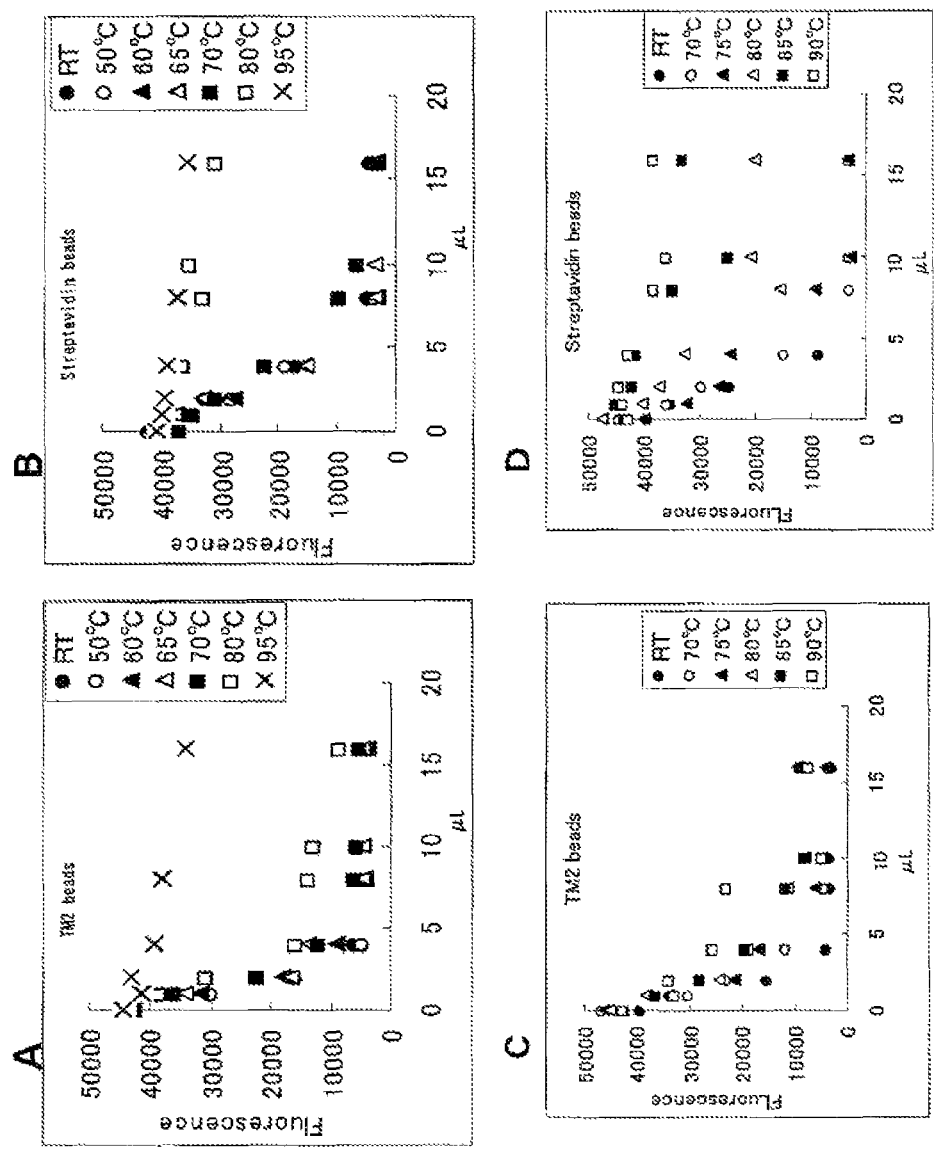
FIG. 5 presents graphs showing the heat resistance (fluorescent biotin-binding activity) of tamavidin 2 magnetic beads (A and C) and commercially available streptavidin magnetic beads (B and D).

The results obtained in Experiment 1 are shown in FIGS. 5A and 5B, while the results obtained in Experiment 2 are shown in FIGS. 5C and 5D. As a result, the TM2 magnetic beads showed no change in their binding to fluorescent biotin at 70° C. or below, compared to the room temperature value, and they retained 75% and 62% activity at 80° C. and 85° C., respectively (FIG. 5A). In contrast, in the commercially available streptavidin magnetic beads, 60% to 80% of their binding to fluorescent biotin disappeared at 80° C. (FIG. 5B). The temperature which caused a 50% reduction in fluorescence intensity decrement compared to the unheated sample was 77.5° C. for streptavidin (Dynal), whereas it was 87.5° C. for tamavidin 2.

Preparation of TM2 Sepharose Beads

Sepharose beads of 34 μm diameter whose surface carboxyl groups were converted into active esters by the action of N-hydroxysuccinimide (NHS) (HiTrap NHS-activated HP (GE Healthcare), 1 mL) were washed with cold 1 mM hydrochloric acid (10 ml) and then further washed with cold ultrapure water (1 ml). These sepharose beads were mixed with 1 ml of 1 mg/ml TM2 which had been dialyzed against 0.2 M sodium bicarbonate buffer (pH 8.3) containing 0.5 M sodium chloride. By shaking at room temperature for 3 hours, TM2 and the sepharose beads were attached to each other. Then, unreacted active groups were eliminated with 50 mM Tris buffer (pH 8.0, 5 ml), and the sepharose beads were blocked with PBS buffer (5 ml) containing 0.5% BSA and 0.05% Tween 20. The sepharose beads were suspended in PBS buffer (1 ml) to complete the desired TM2 sepharose beads.

Heating Test on TM2 Sepharose Beads

By means of fluorescent biotin, the heat resistance of the TM2 sepharose beads was verified. The TM2 sepharose beads were washed with PBS buffer and then heated at room temperature 70° C., 75° C., 80° C., 85° C. or 90° C. for 20 minutes. Solutions were prepared to contain the heated sepharose beads at stepwise concentrations from 0 μL to 16 μL in 150 μL assay buffer. These solutions were each mixed with 50 μl (150 pmol) of a 3 pmol/μl biotin-4-fluorescein solution and allowed to stand at room temperature for 20 minutes, followed by measuring the fluorescence intensity of the supernatant at Ex=460 nm and Em=525 nm with an Infinite M200.

Figure 6:
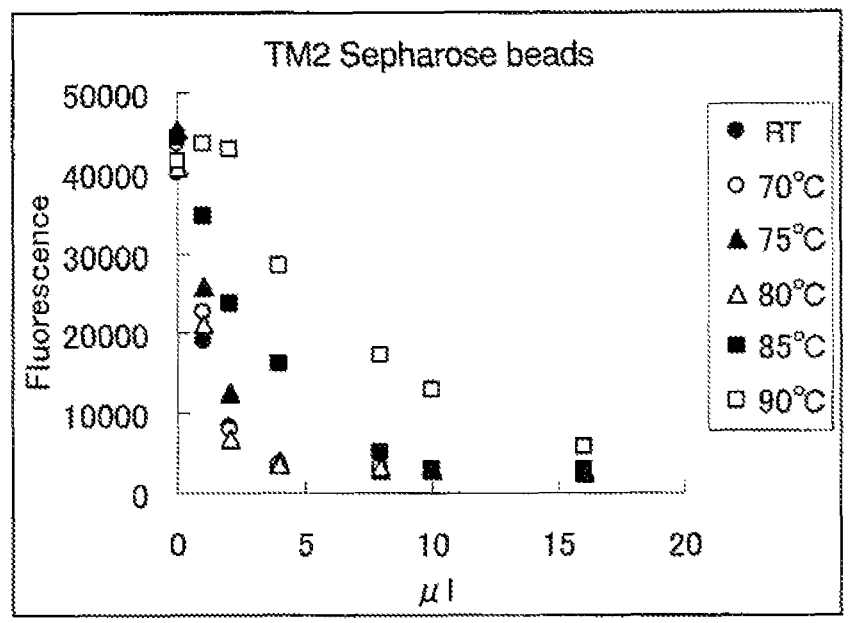
FIG. 6 is a graph showing the heat resistance (fluorescent biotin-binding activity) of tamavidin 2 sepharose beads.

As a result, the TM2 sepharose beads showed no change in their binding to fluorescent biotin at 80° C. or below, compared to the room temperature value, and they retained 64% activity at 85° C. Moreover, the temperature which caused a 50% reduction in fluorescence intensity decrement compared to the unheated sample was 86° C., which was comparable to the heat resistance of the TM2-immobilized magnetic beads (FIG. 6).

Example 2

Tamavidin 1 (TM11)

2-1. Characterization of Tamavidin 1

E. coli Expression and Purification of Tamavidin 1

When DNA encoding tamavidin 1 (SEQ ID NO: 1) was integrated into an expression vector pTrc99A and expressed in E. coli cells, most of the expressed tamavidin 1 molecules were found to be accumulated in a soluble fraction with high expression levels comparable to those of tamavidin 2. Then, a further attempt was made to purify recombinant tamavidin 1 as follows. A pellet of E. coli cells which had been subjected to expression induction and then collected was suspended in 20 mM Kpi pH 7.0, followed by ultrasonication to disrupt the cells. After centrifugation at 15000 rpm for 10 minutes, the supernatant was treated at 70° C. for 10 minutes. After heat treatment, centrifugation was repeated and the supernatant was replaced with 50 mM Tris-HCl pH 7.0, 50 mM NaCl. This sample was applied to an ion exchange column MonoQ HR5/5 (Phaemacia), which had been equilibrated with the same buffer, to collect recombinant tamavidin 1 as a fraction passing through the column. The amount of the protein collected was about 1 mg per 50 mL culture.

Mass Spectrometry

Tamavidin 1 was analyzed by mass spectrometry in the same manner as shown in Example 1. The results observed were: m/z=15961.6 (monomer) and 31922.5 (dimer). The mass of the monomer was in good agreement with the molecular weight of tamavidin 1 as analyzed by SDS-polyacrylamide electrophoresis. On the other hand, tamavidin 1 was incubated with an excess amount of biotin and analyzed for its SDS-polyacrylamide electrophoresis image in comparison with tamavidin 2 treated in the same manner, suggesting that tamavidin 1 was a tetramer. The isoelectric point was calculated to be 6.23 for tamavidin 1 composed of 143 amino acids in total, as analyzed by genetic information processing software GENETYX Ver. 7 (Genetyx Corporation, Japan).

Biotin-Binding Activity

Figure 7:
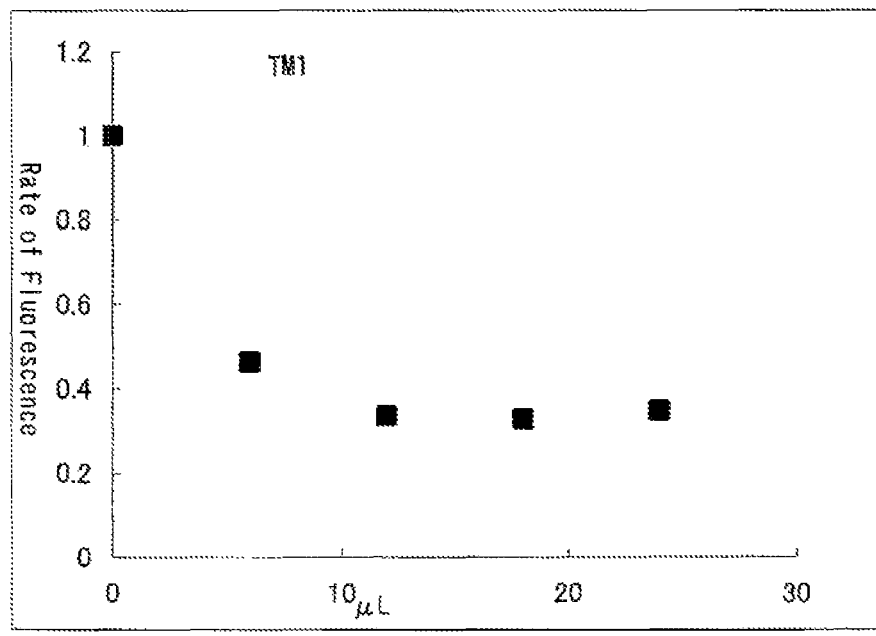
FIG. 7 is a graph showing the fluorescent biotin-binding activity of tamavidin 1.

Fluorescent biotin-binding activity was measured for tamavidin 1 in the above centrifuged supernatant after heat treatment at 70° C. The same procedure as used for tamavidin 2 was repeated for this purpose. Incubation with fluorescent biotin was performed at room temperature. The results obtained are shown in FIG. 7. Tamavidin 1 was found to bind to fluorescent biotin even after treatment at 70° C.

2-2. Heat Resistance of Tamavidin 1

Protein Stability

Purified tamavidin 1 at a concentration of 0.2 μg/μL was heated in 10 μL (2 μg) volumes at room temperature, 50° C., 60° C., 70° C., 80° C., 90° C. or 99° C. for 20 minutes, followed by centrifugation at 15000 rpm for 10 minutes. Each supernatant (soluble protein) was suspended in an equal volume of 2×SDS sample buffer (100 mM Tris-HCl pH 6.8, 12% 2-mercaptoethanol, 2% SDS, 20% glycerol), heated at 95° C. for 10 minutes and then analyzed by SDS-PAGE. Protein bands were detected by CBB staining. Using a Las-3000 system (FUJIFILM), a calibration curve was prepared based on quantification markers (LMW ELECTROPHORESIS CALIBRATION KIT; Pharmacia Biotech) and used to quantify the protein bands. As a result, the temperature which caused a 50% reduction in protein band intensity was 76° C. for tamavidin 1. This result indicated that the heat resistance of tamavidin 1 was 5° C. higher than that of streptavidin mentioned above. Moreover, tamavidin 1 was found to show extremely high heat resistance upon addition of biotin, so that tetramer dissociation was not observed even after treatment at 95° C.

INDUSTRIAL APPLICABILITY

Since tamavidin attached to the solid support of the present invention retains protein stability and biotin-binding activity at a higher temperature range, the solid support of the present invention can be used in assay systems involving treatment at a higher temperature range. Assay systems involving treatment at a higher temperature range allow highly specific separation, concentration, purification, detection and/or capture of substances and thereby contribute to speeding up a series of protocols. Moreover, since tamavidin is produced with higher efficiency than avidin and streptavidin derived from albumen, the solid support of the present invention is also advantageous in terms of cost over commercially available solid supports having a biotin-binding protein attached thereto.

The invention claimed is:

1. A method for separation, concentration, capture, purification and/or detection of a biotin-linked substance, which comprises the following steps:
    1) contacting a solid support with a biotin-linked substance, whereby the biotin-linked substance is bound to the solid support;
    2) washing off contaminants which are not bound to the solid support; and
    3) collecting the biotin-linked substance which is bound to the solid support to thereby separate, concentrate, capture or purify the substance and/or detect the substance
   wherein at least one of the above steps is accomplished under heating conditions of 80° C. to 90° C.,
   wherein the solid support comprising a heat-resistant biotin-binding protein attached thereto retains biotin-binding capacity after heat treatment at 80° C. to 90° C. and/or has biotin-binding capacity under heating conditions of 80° C. to 90° C., and
   wherein the heat-resistant biotin-binding protein is selected from the group consisting of:
    a) a protein which comprises the amino acid sequence shown in SEQ ID NO:4; and
    b) a protein which comprises an amino acid sequence sharing a sequence identity of at least 98% or more with the amino acid sequence shown in SEQ ID NO:4.

2. The method according to claim 1, wherein the heating conditions are set to 80° C. to 85° C.

3. The method according to claim 1, wherein the biotin-linked substance is a biotin-linked nucleic acid.

4. The method according to claim 1, wherein the solid support comprises a material selected from the group consisting of cellulose, polytetrafluoroethylene, nitrocellulose, agarose, dextran, chitosan, polystyrene, polyacrylamide, polyester, polycarbonate, polyamide, polypropylene, nylon, polydivinylidene difluoride, latex, silica, glass, glass fiber, gold, platinum, silver, copper, iron, stainless steel, ferrite, silicon wafer, polyethylene, polyethyleneimine, polylactic acid, resins, polysaccharides, proteins, carbon and combinations thereof.

5. The method according to claim 4, wherein the solid support is albumin.

6. The method according to claim 1, wherein the solid support is selected from the group consisting of beads, magnetic beads, thin films, microtubes, filters, plates, microplates, carbon nanotubes and sensor chips.

\* \* \* \* \*

SEQUENCE LISTING

<160> NUMBER OF SEQ ID NOS: 4

<210> SEQ ID NO 1
<211> LENGTH: 432
<212> TYPE: DNA
<213> ORGANISM: Pleurotus cornucopiae
<220> FEATURE:
<221> NAME/KEY: CDS
<222> LOCATION: (1)..(432)
<223> OTHER INFORMATION:

<400> SEQUENCE: 1

```
atg aaa gac gtc caa tct ctc ctc acc gga acc tgg tac aat gaa ctc      48
Met Lys Asp Val Gln Ser Leu Leu Thr Gly Thr Trp Tyr Asn Glu Leu
1               5                   10                  15 ggc tca aca atg aat ttg act gca aat aaa gac ggt tcg ctc acc gga      96
Gly Ser Thr Met Asn Leu Thr Ala Asn Lys Asp Gly Ser Leu Thr Gly
                20                  25                  30 acg tac cac tcc aac gtc ggc gag gtt ccc cca act tat cac ctt tct     144
Thr Tyr His Ser Asn Val Gly Glu Val Pro Pro Thr Tyr His Leu Ser
            35                  40                  45 ggc cgg tac aac ctc cag ccc ccc tcg ggt caa ggc gtt act ctg gga     192
Gly Arg Tyr Asn Leu Gln Pro Pro Ser Gly Gln Gly Val Thr Leu Gly
        50                  55                  60 tgg gcg gtg tct ttc gaa aac act agt gcg aat gtt cat tct gtc tca     240
Trp Ala Val Ser Phe Glu Asn Thr Ser Ala Asn Val His Ser Val Ser
65                  70                  75                  80 aca tgg agc ggg cag tac ttc tct gaa ccc gcc gag gtg atc ctc acc     288
Thr Trp Ser Gly Gln Tyr Phe Ser Glu Pro Ala Glu Val Ile Leu Thr
                85                  90                  95 cag tgg ctg ttg tca agg agc tct gag cgc gaa gat ttg tgg cag tcc     336
Gln Trp Leu Leu Ser Arg Ser Ser Glu Arg Glu Asp Leu Trp Gln Ser
            100                 105                 110 acc cat gtg ggg cat gat gag ttc agc aag aca aag cca acc aag gag     384
Thr His Val Gly His Asp Glu Phe Ser Lys Thr Lys Pro Thr Lys Glu
        115                 120                 125 aag att gcc cag gct caa ctc ctt cgt cgc ggg ttg aag ttc gag tga     432
Lys Ile Ala Gln Ala Gln Leu Leu Arg Arg Gly Leu Lys Phe Glu
    130                 135                 140
```

<210> SEQ ID NO 2
<211> LENGTH: 143
<212> TYPE: PRT
<213> ORGANISM: Pleurotus cornucopiae

<400> SEQUENCE: 2

```
Met Lys Asp Val Gln Ser Leu Leu Thr Gly Thr Trp Tyr Asn Glu Leu
1               5                   10                  15

Gly Ser Thr Met Asn Leu Thr Ala Asn Lys Asp Gly Ser Leu Thr Gly
                20                  25                  30

Thr Tyr His Ser Asn Val Gly Glu Val Pro Pro Thr Tyr His Leu Ser
            35                  40                  45

Gly Arg Tyr Asn Leu Gln Pro Pro Ser Gly Gln Gly Val Thr Leu Gly
        50                  55                  60

Trp Ala Val Ser Phe Glu Asn Thr Ser Ala Asn Val His Ser Val Ser
65                  70                  75                  80
```

```
Thr Trp Ser Gly Gln Tyr Phe Ser Glu Pro Ala Glu Val Ile Leu Thr
                85                  90                  95

Gln Trp Leu Leu Ser Arg Ser Glu Arg Glu Asp Leu Trp Gln Ser
            100                 105                 110

Thr His Val Gly His Asp Glu Phe Ser Lys Thr Lys Pro Thr Lys Glu
        115                 120                 125

Lys Ile Ala Gln Ala Gln Leu Leu Arg Arg Gly Leu Lys Phe Glu
    130                 135                 140

<210> SEQ ID NO 3
<211> LENGTH: 426
<212> TYPE: DNA
<213> ORGANISM: Pleurotus cornucopiae
<220> FEATURE:
<221> NAME/KEY: CDS
<222> LOCATION: (1)..(426)
<223> OTHER INFORMATION:

<400> SEQUENCE: 3 atg tca gac gtt caa tct tca ctc acc gga acc tgg tac aat gaa ctc     48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga     96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct    144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg    192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg    240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg    288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt    336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa            426
Ala His Ala Gln Leu His Cys Arg Ala Pro Arg Leu Lys
    130                 135                 140

<210> SEQ ID NO 4
<211> LENGTH: 141
<212> TYPE: PRT
<213> ORGANISM: Pleurotus cornucopiae

<400> SEQUENCE: 4

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60
```

```
Trp Ala Val Ser Trp Glu Asn Ser Lys Ile His Ser Ala Thr Thr Trp
 65              70              75              80

Ser Gly Gln Phe Phe Ser Glu Ser Ser Pro Val Ile Leu Thr Gln Trp
             85              90              95

Leu Leu Ser Ser Ser Thr Ala Arg Gly Asp Val Trp Glu Ser Thr Leu
            100             105             110

Val Gly Asn Asp Ser Phe Thr Lys Thr Ala Pro Thr Glu Gln Gln Ile
        115             120             125

Ala His Ala Gln Leu His Cys Arg Ala Pro Arg Leu Lys
    130             135             140
```